United States Patent [19]
Engle

[11] Patent Number: 5,072,294
[45] Date of Patent: Dec. 10, 1991

[54] METHOD AND APPARATUS FOR ANALYZING A BODY HAVING A MARKER LOCATED THEREON

[75] Inventor: Gary L. Engle, Fair Oaks, Calif.

[73] Assignee: Loredan Biomedical, Inc., Davis, Calif.

[21] Appl. No.: 652,296

[22] Filed: Feb. 5, 1991

Related U.S. Application Data

[63] Continuation of Ser. No. 362,735, Jun. 7, 1989, abandoned.

[51] Int. Cl.$^5$ ............................................. H04N 7/18
[52] U.S. Cl. ...................................... 358/125; 358/105
[58] Field of Search ............... 358/105, 125, 108, 107, 358/126, 93; 364/516

[56] References Cited

U.S. PATENT DOCUMENTS

| | | | |
|---|---|---|---|
| 3,729,582 | 4/1973 | Deye et al. | 358/126 |
| 3,953,670 | 4/1976 | Prince | 358/125 |
| 4,004,083 | 1/1977 | Norem | 358/125 |
| 4,219,847 | 8/1980 | Pinkney et al. | 358/126 |
| 4,409,661 | 10/1983 | Romanski | 358/125 X |
| 4,549,211 | 10/1985 | Assael et al. | 358/126 |
| 4,609,939 | 9/1986 | Kozawa | 358/125 X |
| 4,843,460 | 6/1989 | LeGuet et al. | 358/125 X |

*Primary Examiner*—Victor R. Kostak
*Attorney, Agent, or Firm*—Townsend and Townsend

[57] ABSTRACT

A video motion analysis system wherein a camera converts an image of a body having illuminated markers placed thereon into a plurality of image frames. Each image frame comprises a plurality of image lines, and each image line comprises a plurality of pixels. An image preprocessor receives the plurality of image lines and detects the occurrence of each marker in each image line. This is done by comparing each pixel amplitude value to a threshold value and indicating when the pixel amplitude value exceeds the threshold value. When a pixel amplitude value exceeds the threshold value, an offset value representing the difference between the pixel amplitude value and the threshold value is added to a running total of amplitude values for the detected marker. Similarly, the offset value is used to calculate the moment value for each pixel in each marker based on the position of the pixel in the scan line. The calculated moment value is added to a running total of moment values for the detected marker. The amplitude and moment sums for each series of pixels for each marker in each image line are passed to a signal processor which groups the amplitude and moment sums for each marker together. The grouped values are used to calculate a centroid value for each marker. Centroid calculation is performed in real time and the resulting values are provided to a master CPU for further processing.

34 Claims, 5 Drawing Sheets

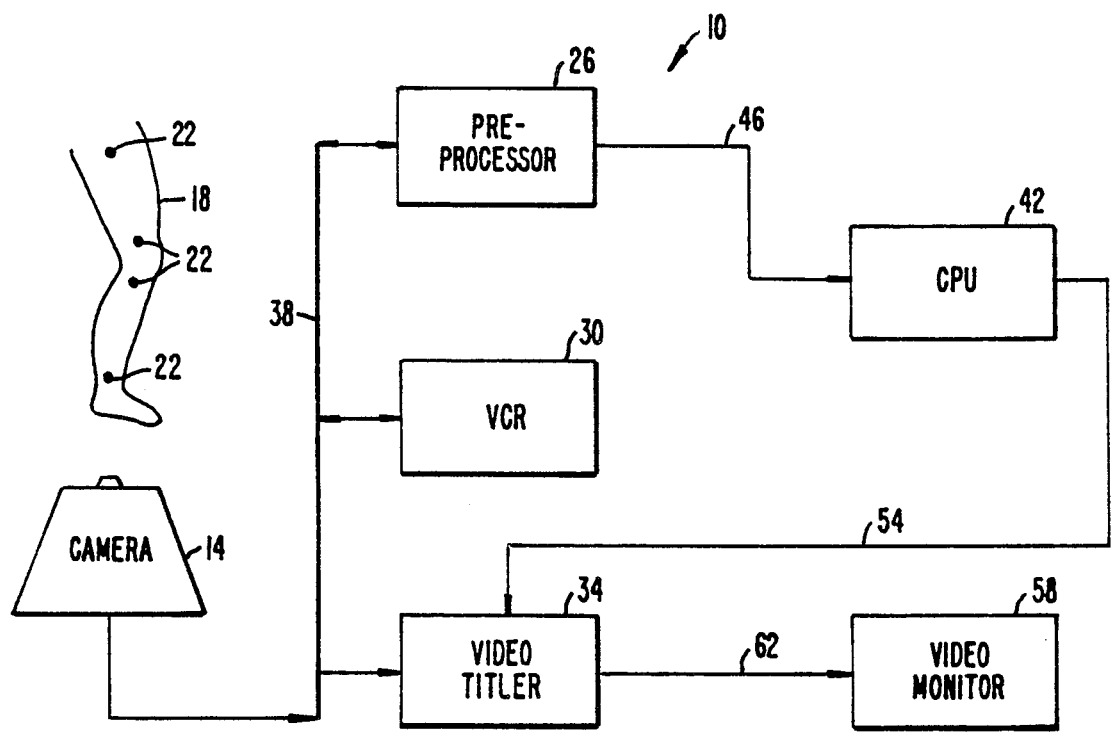
FIG._1.
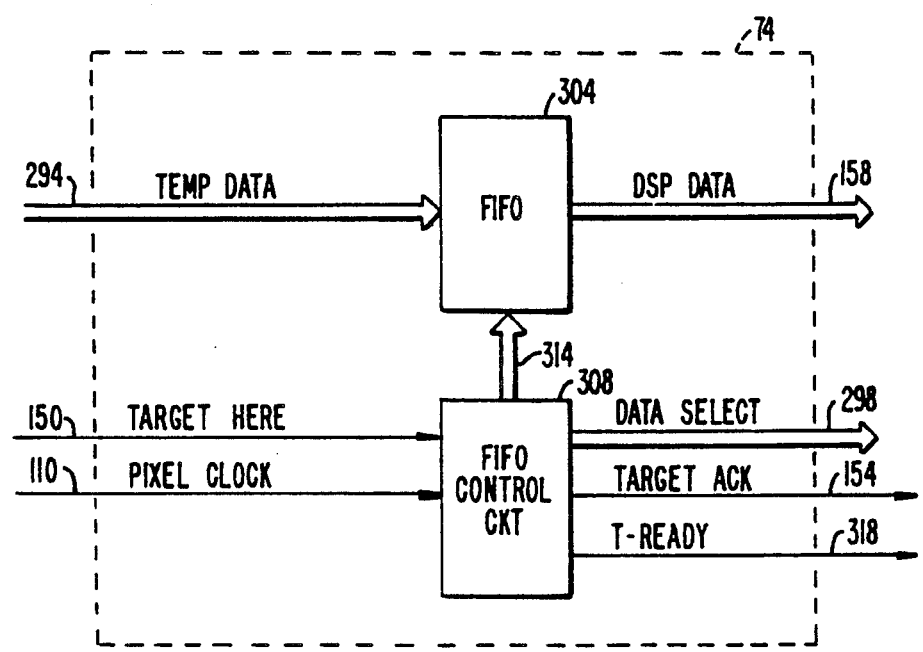
FIG._5.

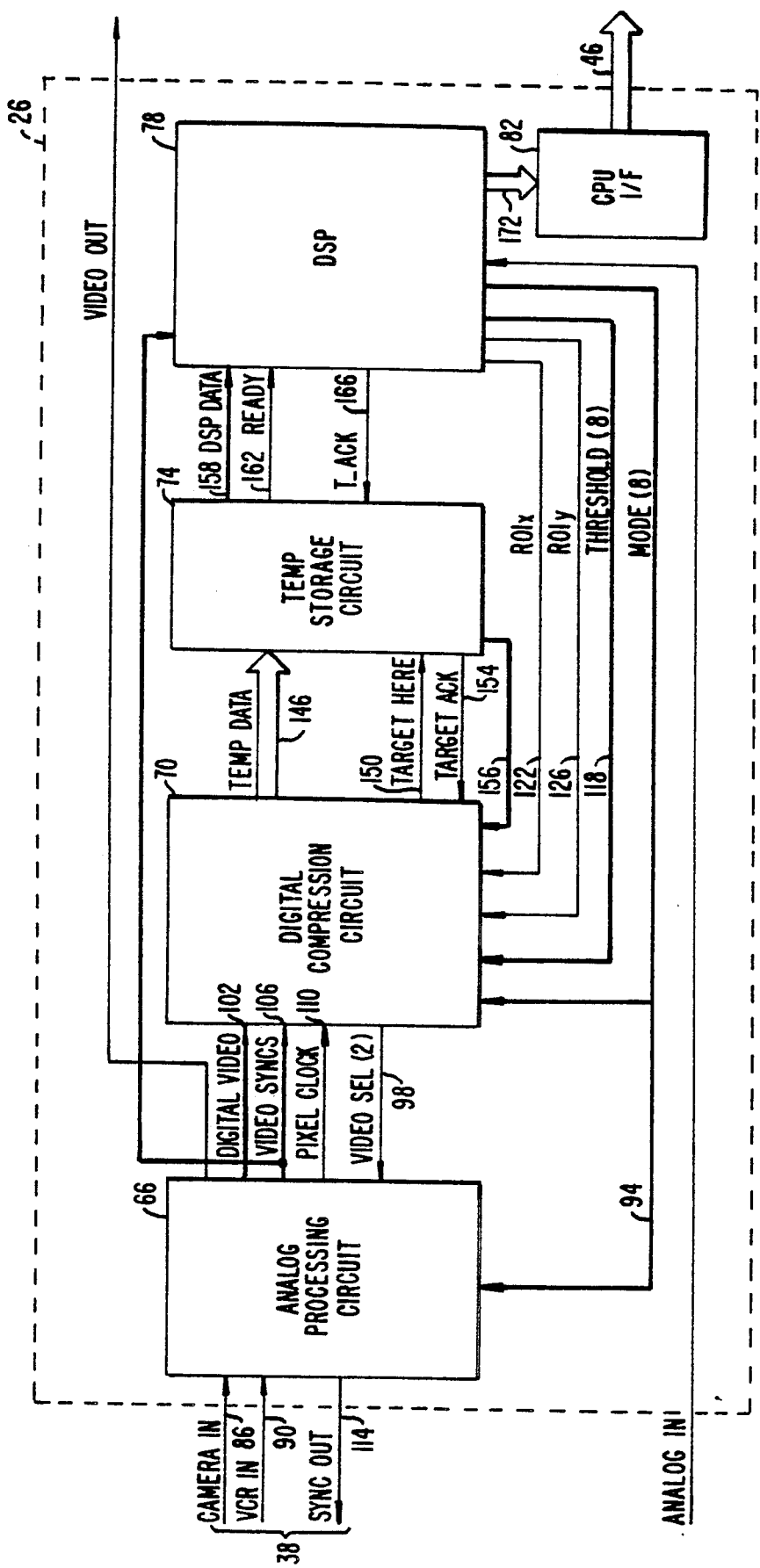
FIG._2.

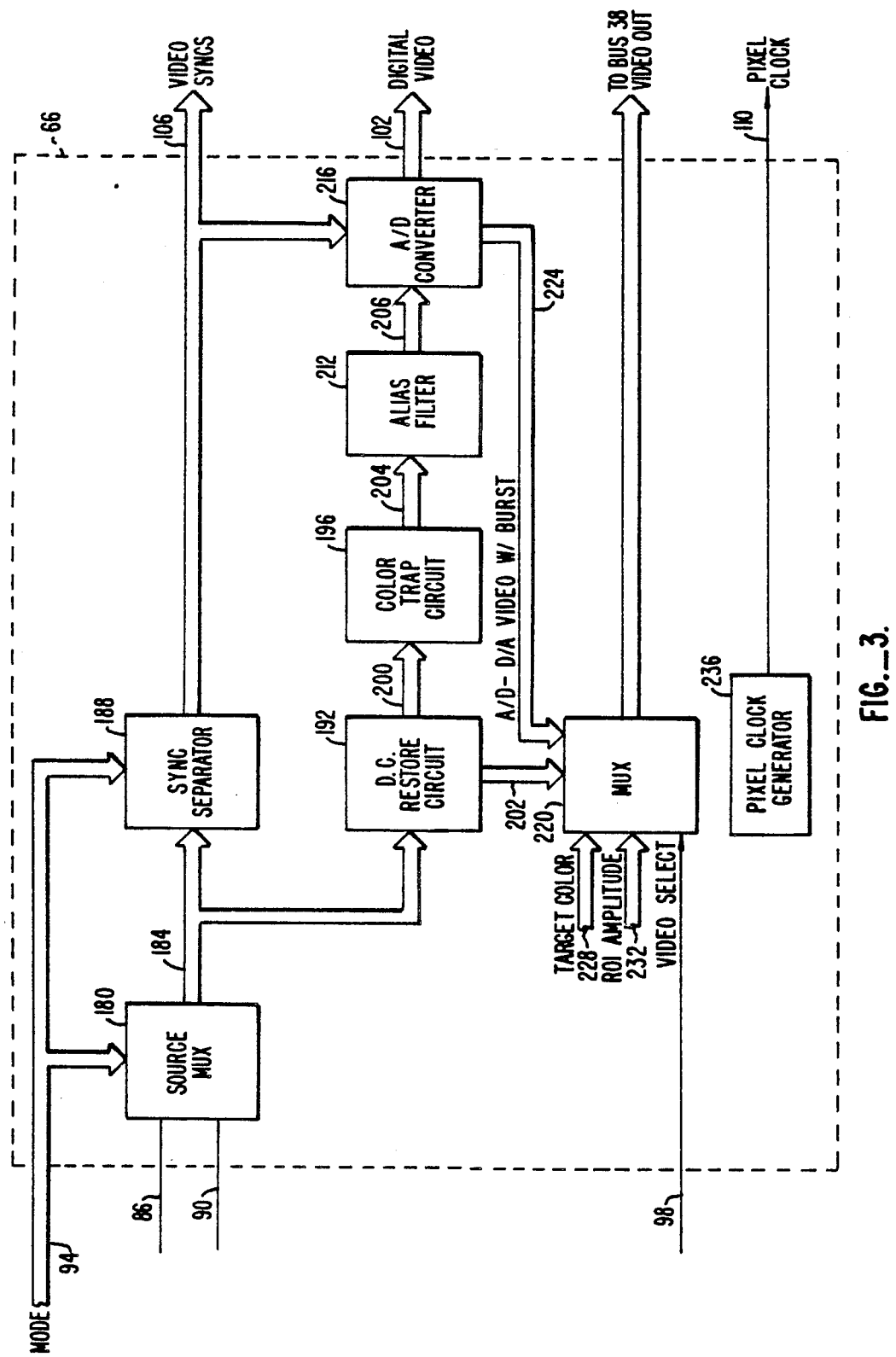

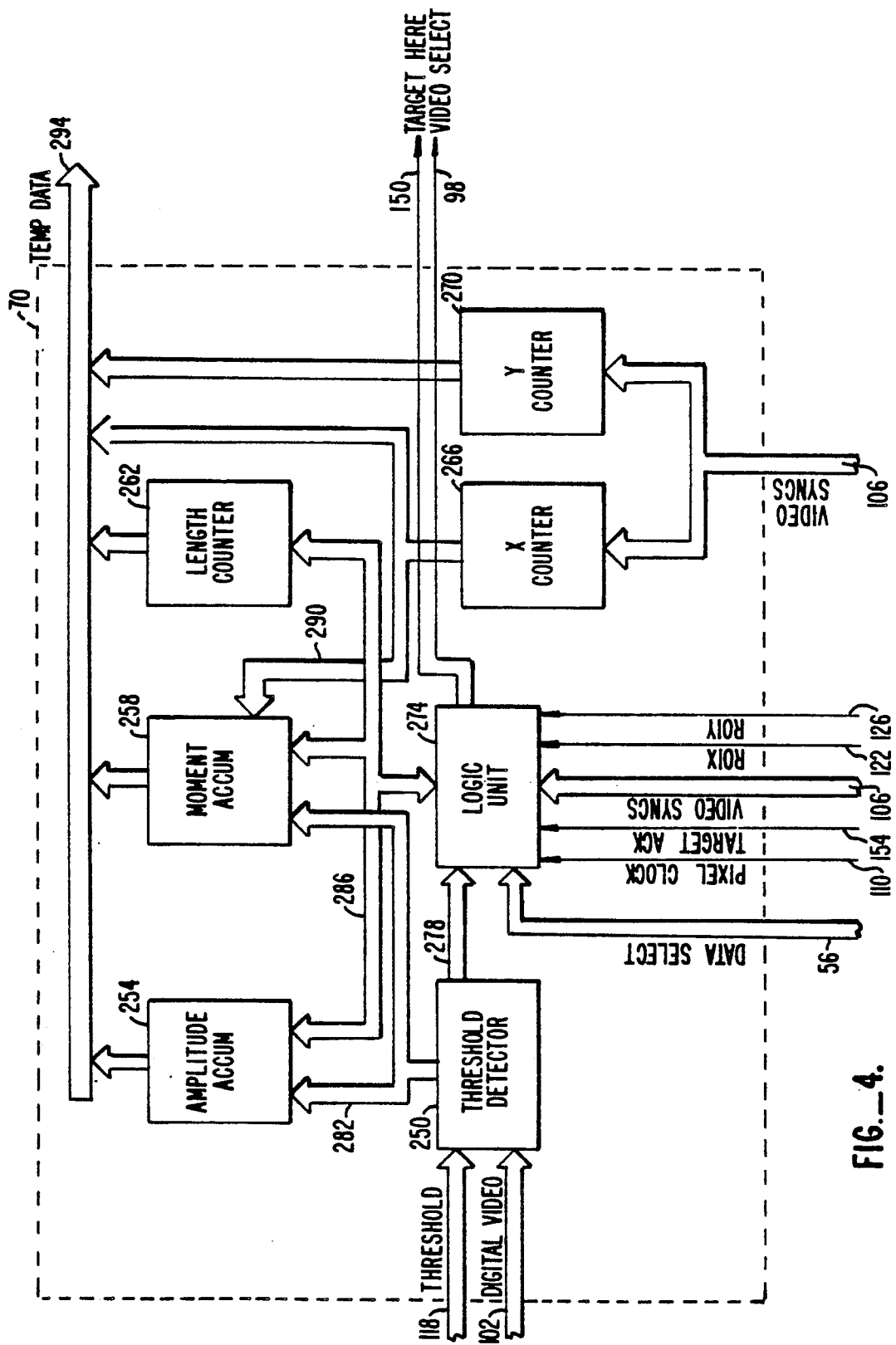
FIG._4.

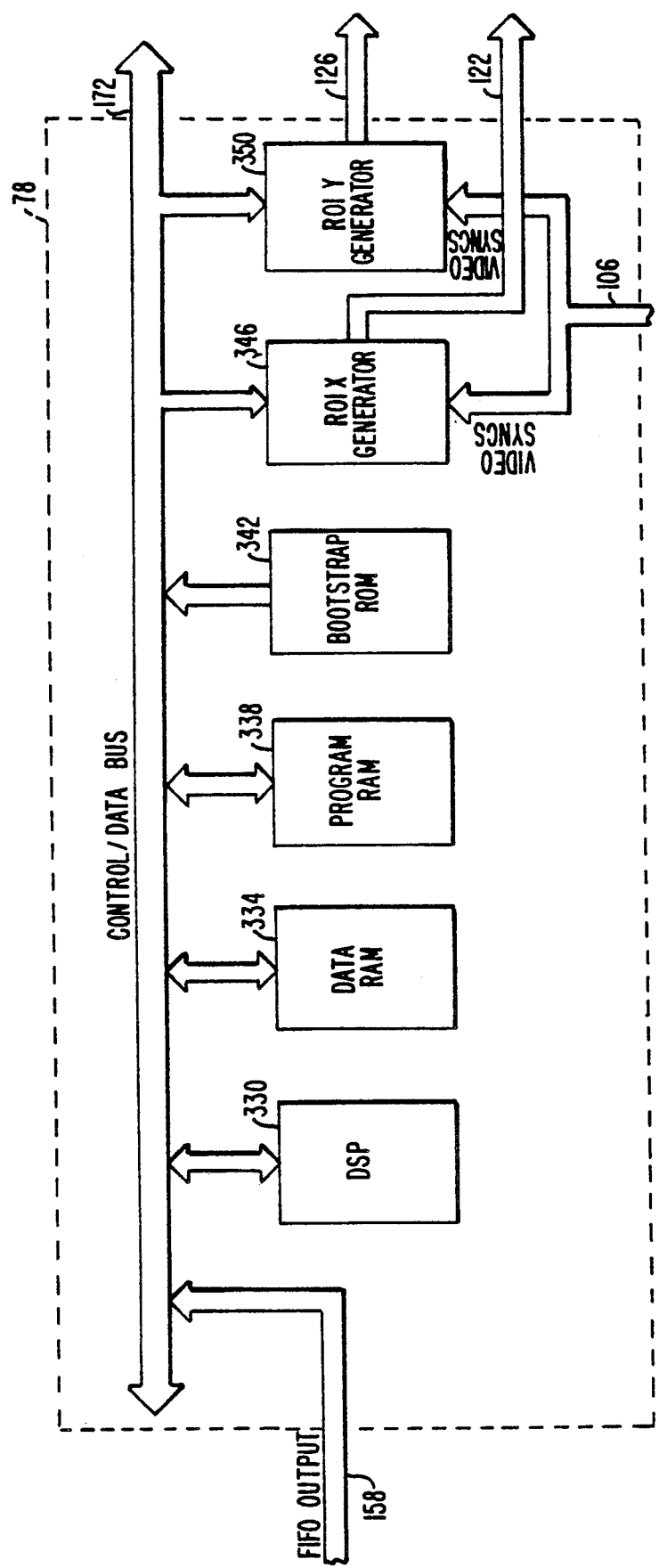
FIG._6.

METHOD AND APPARATUS FOR ANALYZING A BODY HAVING A MARKER LOCATED THEREON

This is a division of application Ser. No. 07/362,735, filed June 7, 1989, now abandoned.

BACKGROUND OF THE INVENTION

This invention relates to motion analysis systems and, more particularly, to an apparatus for analyzing a body having an illuminated marker placed thereon.

Analysis of the biomechanics of human movement is performed in a number of ways. In the past, markers attached to anatomical landmarks on the subject were filmed, and then the markers were hand digitized to determine their position in free space. However, with data rates as high as 500–1,000 pictures per second, the process was very time consuming. The excessive time resulted in high analysis costs and excessive delays before final results were obtained.

In recent years the development of video cameras with high frame rates and shuttered input have spurred the development of automated motion analysis systems. With such cameras, visual information is immediately available as an electric signal that can be conveniently stored on video tape and thereafter made available for analysis by computer. In one system, not necessarily in the prior art, infrared light emitting diodes are placed on anatomical sites on a patient. The diodes are turned on in sequence by a host computer and sensed by a camera. However, reflections of the radiation emitted by the diodes off walls, etc., tend to confound the acquisition system. Furthermore, the patient is forced to be cabled to the system, and this inhibits mobility. Some systems use telemetry to turn on the diodes. However, telemetry systems typically are not a reliable means of information transfer.

In another system, also not necessarily in the prior art, illuminated markers are placed on anatomical sites on a patient, and an image preprocessor derives the marker information from a scanned image of the patient. The markers are detected by comparing the amplitude value of each pixel in the image scan lines to a threshold value. When the amplitude of a pixel exceeds the threshold value, the position of the pixel in the scan line is saved so that the marker may be reproduced by a master CPU on a display screen and used in the motion analysis algorithms. However, measurement resolution is often inadequate for clinical gait studies in part because a pixel with an amplitude barely greater than the threshold value is processed the same as pixel values which greatly exceed the threshold value. Furthermore, because the raw data must typically be processed by the master CPU, operation is overly complex, slow, and frequently requires a trained technician in most settings.

SUMMARY OF THE INVENTION

The present invention is directed to a video motion analysis system which is simpler, more accurate and faster than known systems. In one embodiment of the present invention, a camera converts an image of a body having illuminated markers placed thereon into a plurality of image frames. Each image frame comprises a plurality of image lines, and each image line comprises a plurality of pixels. An image preprocessor receives the plurality of image lines and detects the occurrence of each marker in each image line. This is done by comparing each pixel amplitude value to a threshold value and indicating when the pixel amplitude value exceeds the threshold value. When a pixel amplitude value exceeds the threshold value, an offset value representing the difference between the pixel amplitude value and the threshold value is added to a running total of amplitude values for the detected marker. Similarly, the offset value is used to calculate the moment value for each pixel in each marker based on the position of the pixel in the scan line. The calculated moment value is added to a running total of moment values for the detected marker. The use of offset amplitude values greatly increases measurement accuracy because the contribution of each pixel to the amplitude and moment sums depends on the pixel's brightness.

The amplitude and moment sums for each series of pixels for each marker in each image line are passed to a signal processor which groups the amplitude and moment sums for each marker together. The grouped values are used to calculate a centroid value for each marker. Centroid calculation is performed in real time and the resulting values are provided to a master CPU for further processing. By providing the centroid values to the host computer, it relieves the host computer of the burden of calculating the centroids itself. Consequently, the speed of image processing is greatly increased, requires far fewer CPU resources, and this in turn results in a cheaper and more compact product.

BRIEF DESCRIPTION OF THE DRAWINGS

FIG. 1 is a block diagram of a video motion analysis system according to the present invention.

FIG. 2 is a block diagram of a particular embodiment of the image preprocessor of FIG. 1 according to the present invention.

FIG. 3 is a block diagram of a particular embodiment of the analog processing unit of FIG. 2 according to the present invention.

FIG. 4 is a block diagram of a particular embodiment of the digital compression circuit of FIG. 2 according to the present invention.

FIG. 5 is a block diagram of a particular embodiment of the temporary storage circuit of FIG. 2 according to the present invention.

FIG. 6 is a block diagram of a particular embodiment of the digital signal processor of FIG. 2 according to the present invention.

DETAILED DESCRIPTION OF THE PREFERRED EMBODIMENTS

FIG. 1 is block diagram of a video motion analysis (VMA) system 10 according to the present invention. VMA system 10 includes a camera 14 for converting an image of a body 18 having a plurality of illuminated (e.g. retroreflective) markers 22 placed thereon into a plurality of image frames. Each image frame comprises a plurality of image lines, and each image line comprises a plurality of pixels. Camera 14 communicates each image line to a preprocessor 26, a video cassette recorder (VCR) 30 and a video titler 34 over a bus 38. Preprocessor 26 locates each marker 22, calculates the position and centroid of each marker in real time, and passes the position and centroid data to a master CPU 42 over a bus 46. For real time monitoring of marker detection, preprocessor 26 communicates conditioned image data to video titler 34 over bus 38. VCR 30 is optionally provided for permanently storing copies of the image. VCR 30 may communicate the image data to preprocessor 26 and video titler 34 over bus 38 for processing and/or playback at a later time.

In this embodiment, CPU 42 is an IBM model 30/286 computer. CPU 42 formats the centroid data for a video overlay and communicates the formatted data to video titler 34 over a bus 54. The overlay image may comprise a stick figure of body 18 or some other desired image. Video titler 34 thereafter superimposes the overlay image on the conditioned image data from preprocessor 26 and communicates the composite image to a video monitor 58 over a bus 62. This allows real time confirmation of proper thresholding and centroid calculation. CPU 42 stores the centroid information so that the overlay images may be processed and played back at a later time.

FIG. 2 is a more detailed block diagram of preprocessor 26. Preprocessor 26 includes an analog processing circuit 66, a digital compression circuit 70, a temporary storage circuit 74, a digital signal processing circuit (DSP) 78, and a CPU interface 82.

Analog processing circuit 66 receives camera video data from bus 38 on a camera input line 86; VCR video data from bus 38 on a VCR input line 90; mode select signals from DSP 78 over a mode bus 94; and video select signals from digital compression circuit 70 over a video select line 98. Analog processing circuit 66 conditions and digitizes the analog video input and provides digital video information to digital compression circuit 70 over a digital video bus 102; video sync information to digital compression circuit 70 and DSP 78 over a sync bus 106; and pixel clock pulses to digital compression circuit 70 over a pixel clock line 110. Analog processing circuit 66 provides internally generated sync information to bus 38 over a sync line 114 for controlling the operation of VCR 30 in playback mode. To facilitate real time monitoring of the operation of preprocessor 26, analog processing circuit 66 provides conditioned video signals to bus 38 (and hence video titler 34) over a video out bus 116. The conditioned video signals comprise the original input video with or without the markers and the region of interest (ROI) highlighted.

Digital compression circuit 70 receives the video information from analog processing circuit 66 over digital video bus 102; the video sync information from analog processing circuit 66 over sync bus 106; the pixel clock pulses from analog processing circuit 66 over pixel clock line 110; the mode signals from DSP 78 on mode bus 94; threshold value signals from DSP 78 over a threshold bus 118; ROIX signals from DSP circuit 78 over a ROIX line 122; and ROIY signals from DSP circuit 78 over a ROIY line 126. The signals on ROIX line 122 and ROIY line 126 define where digital compression circuit 70 looks for markers. When the signal on either of these lines is inactive, the input video data is not processed. Digital compression circuit detects the pixels within the ROI, indicated by the signals on ROIX line 122 and ROIY line 126, that exceed the amplitude threshold indicated by the signals on threshold bus 118. This indicates the occurrence of a marker in the image. Digital compression circuit then encodes the pixel amplitudes into quantities that can be used by DSP 78 to calculate centroids of pixel groups. The quantities calculated by digital compression circuit 70 include an amplitude sum, a moment sum, a marker length, a Y value, and an X-end value (i.e. the horizontal end-of-marker position). These values are communicated to temporary storage circuit 74 over a temp data bus 146.

Once these values have been calculated for a group of pixels associated with a particular marker, digital compression circuit 70 provides a marker here signal to temporary storage circuit 74 over a line 150 for informing temporary storage circuit 74 that there is marker data to be stored, and temporary storage circuit 74 provides a marker ACK signal on a line 154 to digital compression unit 70 when the marker information has been stored. Temporary storage circuit 74 provides signals on a data select bus 156 to control which values are communicated from digital compression circuit 70 at any given time.

Temporary storage circuit 74 buffers the data provided by digital compression circuit 70 so that the data flow can be handled by DSP circuit 78. The data stored in temporary storage circuit 74 is communicated to DSP circuit 78 over a DSP data bus 158. Temporary storage circuit 74 indicates when data is available on DSP data bus 158 using signals on a ready line 162. DSP circuit 78 acknowledges the receipt of data from temporary storage circuit 74 by signals provided on a T-ACK line 166.

DSP circuit 78 receives a package of marker information from temporary storage circuit 74, groups the data for each marker together, and calculates a centroid for each marker. The centroid data then may be communicated to CPU interface 82 over a bus 172 and thereafter to CPU 42 over bus 46.

FIG. 3 is a more detailed block diagram of analog processing circuit 66. Analog processing circuit 66 includes a source multiplexer 180 which receives mode signals on mode bus 94, camera data on camera input line 86, and VCR data on VCR input line 90. Source MUX 180 selects the data from one of camera input line 86 or VCR input line 90 in response to signals on mode bus 94 and communicates the selected data on a selected data bus 184 to a sync separator 188 and to a DC restore circuit 192. Sync separator 188 derives the sync information off the composite video input and provides the sync information on video sync bus 106. Sync separator 188 includes a sync generator for generating sync information when desired. Whether or not sync separator 188 derives the sync signals from the composite videos or generates its own sync signals is determined by the signals received on mode bus 94. The derived sync information is used when the source cannot be synchronized externally (e.g. a VCR).

DC restore circuit 192 insures that the incoming video is at the proper DC level even if it has been AC coupled. This is done by sampling the video at the back porch (i.e. the region between the synchronizing pulse trailing edge and the blanking pulse trailing edge) and using the sample data as a reference to be subtracted from the video for the upcoming horizontal line. The restored video is communicated to a color trap circuit 196 over a bus 200 and to a multiplexer 220 over a bus 202. Color trap circuit 196 includes a notch filter for providing a 20 dB reduction at the color sub-carrier frequency. This is particularly useful if the source camera is an NTSC or similar color camera wherein there is color information at 3.58 MHz which may interfere with the amplitude detection of markers. If the camera is S-VHS compatible or monochrome, this filter preferably is bypassed to improve spacial resolution by allowing full bandwidth operation. The video data then is communicated to an alias filter 212. Alias filter 212 is a three pole low pass passive filter that reduces the bandwidth of the source signal prior to digitization. This filter is optional and is used primarily for noise suppression. The filtered data is communicated to an A/D converter 216 over a bus 206.

In this embodiment, A/D converter 216 is a Samsung KSX 3100 converter which has DC restore circuit 212 integrally formed therewith, so a separate DC restore circuit 192 is unnecessary. A/D converter 216 provides the digitized video on digital video bus 102. Additionally, A/D converter 216 provides analog video with burst information added (from sync bus 106) to multiplexer 220 over a bus 224. Multiplexer 220 selects from among DC restored input video received over bus 202, analog video with color burst received over bus 224, marker color highlight information received over a bus 228, and ROI highlight information over a bus 232. The selection is made in response to the signals received over video select line 98. The selected data is output to bus 38 for real time monitoring of the image data.

Analog processing circuit 66 also includes a pixel clock generator 236 for generating the pixel clock pulses on pixel clock line 110.

FIG. 4 is a more detailed block diagram of digital compression circuit 70. Digital compression circuit 70 comprises a threshold detector 250 for detecting the occurrence of each marker in the incoming video data; an amplitude accumulator 254 for summing offset amplitude values for each pixel in each marker; a moment accumulator 258 for summing the moment values for each pixel in each marker; a length counter 262 for counting the length of each marker on each image line; an X counter 266 for counting the X location of each pixel along each image line; a Y counter 270 for counting which image line is being processed; and a logic unit 274. Logic unit 274 controls the operation of the other components and provides the appropriate hand shake signals to temporary storage circuit 74.

Threshold detector 250 receives the digital video over digital video bus 102 and the threshold amplitude value over threshold bus 118 and compares each pixel in each image line to the threshold value. When a given pixel amplitude exceeds the threshold value, a marker flag signal is provided on a marker flag bus 278 to logic unit 274. Threshold detector 250 calculates the difference between the pixel amplitude and the threshold value to produce an offset amplitude value which is provided to amplitude accumulator 254 and moment accumulator 258 over an amplitude bus 282. The accumulators 254, 258 and length counter 262 are enabled by logic unit 274 using signals received over a control bus 286. Logic unit 274 insures that only markers detected within the region of interest, as determined by the signals received on ROIX line 122 and ROIY line 126, are processed. If enabled, amplitude accumulator 254, moment accumulator 258 and length counter 262 begin and continue operation as long as the marker flag is being provided from threshold detector 250 over bus 278. Amplitude accumulator 254 sums the offset amplitude value for each pixel, whereas moment accumulator 256 sums the product of the offset amplitude value with the value of X counter 266 received over a bus 290. Logic unit 274 provides signals on video select line 98 to analog processing circuit 66 so that each marker and region of interest may be appropriately highlighted on monitor 58.

Whenever a pixel amplitude value fails to exceed the threshold amplitude value, the marker flag signal on bus 278 is negated for indicating to logic unit 274 that the end of a marker on a particular line has been detected. When this occurs, a signal is provided on marker here line 150 for informing temporary storage circuit 74 that digital compression circuit 70 has marker data to transfer. Thereafter, the values in amplitude accumulator 254, moment accumulator 258, length counter 262, X counter 266, and Y counter 270 are transferred to temporary storage circuit 74 over a temp data bus 294 in response to multiplexing signals received over a data select bus 298. After temporary storage circuit 74 has stored the marker data, it communicates the acknowledgement signal over marker ACK line 154.

FIG. 5 is a more detailed block diagram of temporary storage circuit 74. Temporary storage circuit 74 comprises a fifo memory 304 and a fifo control circuit 308. Fifo 304 stores the amplitude, moment, length, X and Y values received over temp data bus 294 and subsequently communicates these values to DSP circuit 78 over DSP data bus 158. In this embodiment, fifo 304 is a 1K by 9 fifo memory for buffering the data between digital compression circuit 70 and DSP circuit 78. The speed of fifo 304 determines the minimum time between marker endings, because all the values in the holding registers should be stored before they are loaded again at the end of the next marker. Fifo control circuit 308 receives the marker here signals on marker here line 150 and the pixel clock signals on pixel clock line 110 and controls the operation of fifo 304 using signals communicated to fifo 304 over a fifo control bus 314. When the marker here signal is received over line 150, the data select signals are provided on data select line 298 for sequencing through the holding registers in digital compression circuit 70. When all data from digital compression circuit 70 for a particular marker is stored in fifo 304, the acknowledgement signal is generated on marker ACK line 154, and fifo control circuit 308 generates a ready signal on a ready line 318 for informing DSP circuit 78 that fifo 304 has data to be processed.

FIG. 6 is a more detailed block diagram of DSP circuit 78. DSP circuit 78 comprises a DSP processor, which in this embodiment is part number DSP 56001 from Motorola Inc. A data RAM 334 provides working storage for DSP 330 (in addition to the on chip data RAM within DSP 330). A program RAM 338 provides the programming for DSP 330, and a bootstrap ROM 342 provides the initialization program for DSP 330. An ROIX generator 346 and an ROIY generator 350 receive the video sync information over bus 106 and ROI control information from CPU 42 over CPU interface bus 172. ROIX generator 346 and ROIY generator generate the appropriate ROIX and ROIY signals over ROIX line 122 and ROIY line 126, respectively. DSP circuit 78 communicates with CPU interface 82 and CPU 42 over CPU interface bus 172.

In operation, camera 14 converts an image of body 18 into a plurality of image lines wherein each image line comprises a plurality of pixels. Analog processing circuit 66 digitizes each pixel in each image line and provides the pixel data to digital compression circuit 70. Digital compression circuit 70 compares each pixel with the threshold value received over threshold bus 118 and, if a pixel amplitude value exceeds the threshold, begins accumulating the offset amplitude and moment values for each pixel. This continues as long as the pixel amplitudes exceed the threshold. When a pixel amplitude no longer exceeds the threshold, the end of a marker on the current image line has been reached and digital compression circuit 70 generates a signal on marker here line 150 to temporary storage circuit 74.

Temporary storage circuit 74 thereafter stores the marker data in fifo 304 and acknowledges the storage operation to digital compression circuit 70 by a signal on marker ACK line 154. Once the data is stored in fifo 304, temporary storage circuit 74 produces a signal on ready line 162 to DSP circuit 78 for informing DSP circuit 78 that there is marker data to be processed. DSP circuit 78 takes the amplitude, moment, and length values for each marker in each line, and, with the aid of the X-end values from X counter 266 and the Y values from Y counter 270, groups the marker data for a plurality of image lines together and calculates the centroid for each marker. The algorithm used for calculating the centroid once markers have been grouped together is as follows:

$$Xc = \frac{\Sigma(SXMy)}{\Sigma SMy} \quad Yc = \frac{\Sigma(y*SMv)}{\Sigma SMy}$$

where all summations ($\Sigma$) are done over the vertical extent (y) of the marker group. SXMy is the x moment accumulation of the marker for each line, y is the line number of the marker and SMy is the amplitude accumulation of the marker for each line.

Xc and Yc are the centroid values sent to the host. The normalization factor ($\Sigma SMy$) may be included with the centroid values if desired.

While the above is a complete description of the preferred embodiment of the present invention, various modifications may be employed. For example, there is enough storage for an entire study of centroid information in the data space of the DSP, but in this embodiment the centroid data is sent to the host (e.g. on a DMA channel) while it is being calculated. Alternatively, processed centroid information from the host may be sent back to the DSP for filtering or reconstruction, then sent back to the host for further processing or display. Consequently, the scope of the invention should not be limited except as described in the claims.

We claim:

1. An apparatus for analyzing a body having a marker that is distinguishable from the body located thereon comprising:
   image line receiving means for receiving a plurality of image lines which form an image frame of the body, each image line comprising a plurality of pixels, each pixel having an amplitude value associated therewith;
   marker detecting means, coupled to the image line receiving means, for detecting the occurrence of the marker in each image line, said marker detecting means including threshold detecting means for detecting when an amplitude threshold value is exceeded by the pixel amplitude value, and marker indicating means, coupled to the threshold detecting means, for providing a marker indicating signal as long as the amplitude threshold value is exceeded by the pixel amplitude value; and
   position calculating means, coupled o the marker detecting means, for calculating a position of the marker in the frame in real time, said position calculating means including amplitude summing means, coupled to the marker indicating means, for summing a pixel amplitude value in response to the marker indicating signal to produce an amplitude sum associated with the detected marker in each image line.

2. The apparatus according to claim 1 further comprising display means, coupled to the position calculating means, for displaying the image, the display means including marker display means for displaying the marker on the image.

3. The apparatus according to claim 1 wherein the marker detecting means further comprises marker discriminating means for detecting the marker only if the marker lies within a selected subset of the image frame.

4. The apparatus according to claim 1 wherein the threshold detecting means further comprises amplitude offset means for calculating the difference in value between the amplitude threshold value and the pixel amplitude value, the difference being termed an amplitude offset value.

5. The apparatus according to claim 4 wherein the position calculating means is coupled to the amplitude offset means, and wherein the amplitude values summed by the position calculating means comprise the amplitude offset values for the detected marker.

6. The apparatus according to claim 5 wherein the position calculating means further comprises:
   horizontal location means for providing a horizontal location for each pixel in each line; and
   horizontal moment summing means, coupled to the marker indicating means, for summing the product of the horizontal location and the amplitude offset value of each pixel in response to the marker indicating signal to produce a horizontal moment sum associated with the detected marker in each image line.

7. The apparatus according to claim 6 wherein the position calculating means further comprises:
   vertical location means for providing a vertical location for the detected marker in each image line; and
   vertical moment summing means, coupled to the vertical location means, for summing the product of the vertical location and the amplitude sum associated with the detected marker in each image line to produce a vertical moment sum associated with the detected marker.

8. The apparatus according to claim 1 wherein the position calculating means calculates a centroid of the region of the image occupied by the marker.

9. The apparatus according to claim 8 wherein the position calculating means further comprises:
   an X-coordinate calculating means, coupled to the horizontal moment summing means and to the amplitude summing means, for calculating an X-coordinate for the marker according to the algorithm:

$$Xc = \frac{\Sigma(SXMv)}{\Sigma SMy}$$

wherein the summations are performed over each image line for which the marker is detected, wherein SXMy is the horizontal moment sum of the marker in each image line, and wherein SMy is the amplitude sum of the marker in each image line.

10. The apparatus according to claim 9 wherein the position calculating means further comprises a Y-coordinate calculating means, coupled to the vertical moment summing means and to the amplitude summing means, for calculating a Y-coordinate for the marker according to the algorithm:

$$Yc = \frac{\Sigma(Y*SMv)}{\Sigma SMy}$$

wherein the summations are performed over each image line for which the marker is detected, and wherein Y*SMy is the vertical moment of the marker in the yth image line.

11. An apparatus for analyzing a body having a plurality of markers that are distinguishable from the body located thereon comprising:
   image line receiving means for receiving a plurality of image lines which form an image frame of the body, each image line comprising a plurality of pixels, each pixel having an amplitude value associated therewith;
   marker detecting means, coupled to the image line receiving means, for detecting the occurrence of the plurality of markers in the plurality of image lines, said marker detecting means including threshold detecting means for detecting when an amplitude threshold value is exceeded by the pixel amplitude value, and marker indicating means, coupled to the threshold detecting means, for indicating the occurrence of each marker in each image line as long as the amplitude threshold value is exceeded by the pixel amplitude value; and
   position calculating means, coupled to the marker detecting means, for calculating the centroids of the plurality of markers in the image frame in real time, said position calculating means including amplitude summing means, coupled to the marker indicating means, for summing a pixel amplitude value in response to the marker indicating signal to produce an amplitude sum associated with each detected marker in each image line.

12. The apparatus according to claim 11 wherein the threshold detecting means further comprises amplitude offset means for calculating the difference in value between the amplitude threshold value and the pixel amplitude value, the difference being termed an amplitude offset value.

13. The apparatus according to claim 12 wherein the position calculating means is coupled to the amplitude offset means, and wherein the amplitude values summed by the position calculating means comprise the amplitude offset values for each detected marker.

14. The apparatus according to claim 13 wherein the position calculating means further comprises:
   horizontal location means for providing a horizontal location for each pixel in each line; and
   horizontal moment summing means, coupled to the marker indicating means, for summing the product of the horizontal location and the amplitude offset value of each pixel in response to the marker indicating signal to produce a horizontal moment sum associated with each detected marker in each image line;
   vertical location means for providing a vertical location for each detected marker in each image line; and
   vertical moment summing means, coupled to the vertical location means, for summing the product of the vertical location and the amplitude sum associated with each detected marker in each image line to produce a vertical moment sum associated with the detected marker.

15. The apparatus according to claim 14 wherein the position calculating means further comprises:
   an X-coordinate calculating means, coupled to the horizontal moment summing means and to the amplitude summing means, for calculating an X-coordinate for each marker according to the algorithm:

$$Xc = \frac{\Sigma(SXMv)}{\Sigma SMy}$$

wherein the summations are performed over each image line for which each marker is detected, wherein SXMy is the horizontal moment sum of each marker in each image line, and wherein SMy is the amplitude sum of each marker in each image line; and
   a Y-coordinate calculating means, coupled to the vertical moment summing means and to the amplitude summing means, for calculating a Y-coordinate for each marker according to the algorithm:

$$Yc = \frac{\Sigma(Y*SMv)}{\Sigma SMy}$$

wherein the summations are performed over each image line for which each marker is detected, and wherein Y*SMy is the vertical moment of the marker in the yth image line.

16. The apparatus according to claim 15 further comprising display means, coupled to the position calculating means, for displaying the image, the display means including marker display means for displaying the marker on the image.

17. The apparatus according to claim 16 wherein the marker detecting means further comprises marker discriminating means for detecting the marker only if the marker lies within a selected subset of the image frame.

18. A method for analyzing a body having a marker that is distinguishable from the body located thereon comprising the steps of:
   receiving a plurality of image lines which form an image frame of the body, each image line comprises a plurality of pixels, each pixel having an amplitude value associated therewith;
   detecting the occurrence of the marker in each image line including the sub-steps of detecting when an amplitude threshold value is exceeded by the pixel amplitude value, and providing a marker indicating signal as long as the amplitude threshold value is exceeded by the pixel amplitude value; and
   calculating a position of the marker in the frame in real time including the sub-step of summing a pixel amplitude value in response to the marker indicating signal to produce an amplitude sum associated with the detected marker in each image line.

19. The method according to claim 18 further comprising the steps of:
   displaying the image; and
   displaying the marker on the image.

20. The method according to claim 19 wherein the marker detecting step further comprises the step of detecting the marker only if the marker lies within a selected subset of the image frame.

21. The method according to claim 18 wherein the threshold detecting step further comprises the step of calculating the difference in value between the amplitude threshold value and the pixel amplitude value, the difference being termed an amplitude offset value.

22. The method according to claim 21 wherein the summed amplitude values comprise the amplitude offset values for the detected marker.

23. The method according to claim 22 wherein the position calculating step further comprises the steps of:
providing a horizontal location for each pixel in each line; and
summing the product of the horizontal location and the amplitude offset value of each pixel in response to the marker indicating signal to produce a horizontal moment sum associated with the detected marker in each image line.

24. The method according to claim 23 wherein the coordinate calculating step further comprises the steps of:
providing a vertical location for the detected marker in each image line; and
summing the product of the vertical location and the amplitude sum associated with the detected marker in each image line to produce a vertical moment sum associated with the detected marker.

25. The method according to claim 24 wherein the position calculating step further comprises the step of calculating a centroid of the region of the image occupied by the marker.

26. The method according to claim 25 wherein the position calculating step further comprises the step of:
calculating an X-coordinate for the marker according to the algorithm:

$$Xc = \frac{\Sigma(SXMy)}{\Sigma SMy}$$

wherein the summations are performed over each image line for which the marker is detected, wherein SXMy is the horizontal moment sum of the marker in each image line, and wherein SMy is the amplitude sum of the marker in each image line.

27. The method according to claim 26 wherein the position calculating step further comprises the steps of:
calculating a Y-coordinate for the marker according to the algorithm:

$$Yc = \frac{\Sigma(Y*SMy)}{\Sigma SMy}$$

wherein the summations are performed over each image line for which the marker is detected, and wherein Y*SMy is the vertical moment of the marker in the yth image line.

28. A method of analyzing a body having a plurality of markers that are distinguishable from the body located thereon comprising the steps of:
receiving a plurality of image lines which form an image frame of the body, each image line comprising a plurality of pixels, each pixel having an amplitude value associated therewith;
detecting the occurrence of the plurality of markers in the plurality of image lines including the substeps of detecting when an amplitude threshold value is exceeded by the pixel amplitude value, and indicating the occurrence of each marker in each image line by providing a marker indicating signal as long as the amplitude threshold value is exceeded by the pixel amplitude value; and
calculating the centroids of the plurality of markers in the image frame in real time including the sub-step of summing a pixel amplitude value in response to the marker indicating signal to produce an amplitude sum associated with each detected marker in each image line.

29. The method according to claim 28 further comprising the steps of:
displaying the image; and
displaying the plurality of markers on the image.

30. The method according to claim 28 wherein the marker detecting step further comprises the step of detecting a marker only if the marker lies within a selected subset of the image frame.

31. The method according to claim 28 wherein the threshold detecting step further comprises the step of calculating the difference in value between the amplitude threshold value and the pixel amplitude value, the difference being termed an amplitude offset value.

32. The method according to claim 31 wherein the summed amplitude values comprise the amplitude offset values for the detected marker.

33. The method according to claim 32 wherein the position calculating step further comprises the steps of:
providing a horizontal location for each pixel in each line;
summing the product of the horizontal location and the amplitude offset value of each pixel in response to the marker indicating signal to produce a horizontal moment sum associated with each detected marker in each image line;
providing a vertical location for the detected marker in each image line; and
summing the product of the vertical location and the amplitude sum associated with the detected marker in each image line to produce a vertical moment sum associated with each detected marker.

34. The method according to claim 33 wherein the position calculating step further comprises the steps of:
calculating an X-coordinate for each marker according to the algorithm:

$$Xc = \frac{\Sigma(SXMy)}{\Sigma SMy}$$

wherein the summations are performed over each image line for which each marker is detected, wherein SXMy is the horizontal moment sum of each marker in each image line, and wherein SMy is the amplitude sum of each marker in each image line; and
calculating a Y-coordinate for each marker according to the algorithm:

$$Yc = \frac{\Sigma(Y*SMy)}{\Sigma SMy}$$

wherein the summations are performed over each image line for which each marker is detected, and wherein Y*SMy is the vertical moment of each marker in the yth image line.

* * * * *